US005770739A

United States Patent [19]
Lin et al.

[11] Patent Number: 5,770,739
[45] Date of Patent: Jun. 23, 1998

[54] NON-AQUEOUS HYDROGEN PEROXIDE COMPLEX

[75] Inventors: Szu-Min Lin; James Archie Swanzy; Paul Taylor Jacobs, all of Arlington, Tex.

[73] Assignee: Johnson & Johnson Medical, Inc., Irvine, Calif.

[21] Appl. No.: 697,547

[22] Filed: Aug. 26, 1996

Related U.S. Application Data

[60] Division of Ser. No. 369,786, Jan. 6, 1995, Pat. No. 5,674,450, which is a continuation-in-part of Ser. No. 264,738, Apr. 28, 1994, abandoned.

[51] Int. Cl.⁶ .................. C07C 209/00; C07D 233/64
[52] U.S. Cl. .................. 548/335.5; 422/29; 423/203; 423/272; 423/306; 524/438; 525/61; 525/387; 525/920; 536/59; 536/69; 548/339.1; 548/519; 548/543; 560/264
[58] Field of Search .................. 422/29; 423/203, 423/272, 306; 524/438; 525/61, 387, 920; 535/59, 69; 548/335.5, 339.1, 519, 543; 560/264; 562/575; 564/38, 61, 63, 153, 215

[56] References Cited

U.S. PATENT DOCUMENTS

| | | | |
|---|---|---|---|
| 2,986,448 | 5/1961 | Gates et al. | 423/415.1 |
| 3,376,110 | 4/1968 | Shiraelf et al. | 423/272 |
| 3,480,557 | 11/1969 | Shiraelf et al. | 252/186 |
| 3,494,726 | 2/1970 | Barasch | 422/29 |
| 3,870,783 | 3/1975 | Hall et al. | 423/415 |
| 4,051,059 | 9/1977 | Bowing et al. | 252/186 |
| 4,169,123 | 9/1979 | Moore et al. | 422/29 |
| 4,169,124 | 9/1979 | Forstrom et al. | 422/29 |
| 4,178,263 | 12/1979 | Priddy | 252/186 |
| 4,437,567 | 3/1984 | Jeng | 206/210 |
| 4,458,009 | 7/1984 | Weyde et al. | 430/350 |
| 4,637,894 | 1/1987 | Smidrkal et al. | 252/186.4 |
| 4,642,165 | 2/1987 | Bier | 203/12 |
| 4,643,876 | 2/1987 | Jacobs et al. | 422/23 |
| 4,717,544 | 1/1988 | Calcaterra et al. | 422/29 |
| 4,744,951 | 5/1988 | Cummings et al. | 422/28 |
| 4,756,882 | 7/1988 | Jacobs et al. | 422/23 |
| 4,889,689 | 12/1989 | Tsao | 422/30 |
| 4,908,188 | 3/1990 | Jefferies, III et al. | 422/111 |
| 4,943,414 | 7/1990 | Jacobs et al. | 422/28 |
| 4,981,662 | 1/1991 | Dougherty | 423/272 |
| 5,008,093 | 4/1991 | Merianos | 423/272 |
| 5,008,106 | 4/1991 | Merianos et al. | 424/80 |
| 5,030,380 | 7/1991 | Moschner et al. | 252/186.7 |
| 5,077,047 | 12/1991 | Biss et al. | 525/387 |
| 5,087,418 | 2/1992 | Jacob | 422/23 |
| 5,115,166 | 5/1992 | Campbell et al. | 315/111.12 |
| 5,122,354 | 6/1992 | Tsuji et al. | 423/272 |
| 5,183,901 | 2/1993 | Login et al. | 548/543 |
| 5,206,385 | 4/1993 | Login et al. | 548/543 |
| 5,211,927 | 5/1993 | Itani et al. | 423/272 |

FOREIGN PATENT DOCUMENTS

| | | |
|---|---|---|
| 1 681 860 A1 | 1/1989 | Russian Federation . |
| 1681860 | 10/1991 | U.S.S.R. . |
| 2223680 | 4/1990 | United Kingdom . |
| WO 92/17158 | 10/1992 | WIPO . |

OTHER PUBLICATIONS

Lu et al., "The Crystal Structure of the Urea–Hydrogen Peroxide Addition Compound CH(NH$_2$)$_2$H$_2$ O$_2$" Jun. 1941, pp. 1507–1513.

House et al., "A TG study of the decomposition of ammonium floride and ammonium bifluoride" *Chemical Abstracts*, Abstract #95:139424w, vol. 95, p. 444, 1981.

Windholz et al., Editors, Ammonium Flouride, *The Merck Index*, p. 78, 1983.

Titova, K.V., et al., "Potassium Carbonate Peroxyhydrate (K$_2$CO$_3$3H$_2$O$_2$)" *Zhurnal Neorganicheskoi Khimii*, vol. 30, Issue 9, pp. 2222–2227, 1985.

N. Irving Sax, Editor, *Dangerous Properties of Industrial Materials,*, Fourth Edition, pp. 772–817, 1975.

*Primary Examiner*—Richard L. Raymond
*Attorney, Agent, or Firm*—Knobbe, Martens, Olson & Bear, LLP

[57] ABSTRACT

An apparatus and process for hydrogen peroxide vapor sterilization of medical instruments and similar devices make use of hydrogen peroxide vapor released from a substantially non-aqueous organic hydrogen peroxide complex, such as a urea-peroxide complex. Optionally, a plasma can be used in conjunction with the vapor. A method for preparing substantially non-aqueous hydrogen peroxide complexes is also provided. These complexes are useful as a source of peroxide vapor in hydrogen peroxide vapor sterilizers and as a component of self-sterilizing packaging materials.

19 Claims, 4 Drawing Sheets

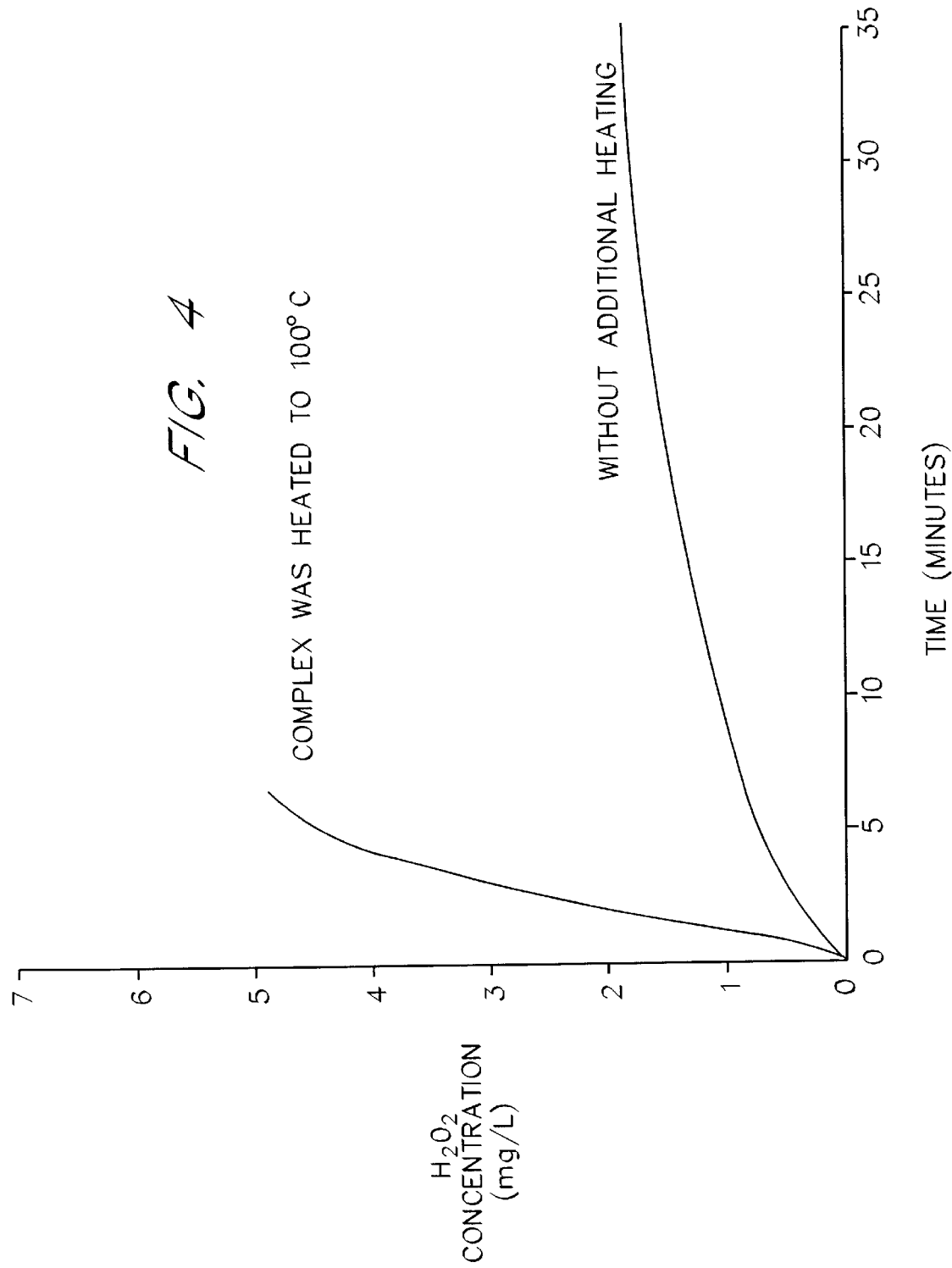

NON-AQUEOUS HYDROGEN PEROXIDE COMPLEX

RELATED APPLICATIONS

This application is a divisional application of U.S. patent application Ser. No. 08/369,786, filed Jan. 6, 1995, now U.S. Pat. No. 5,674,450, which is a continuation-in-part application of U.S. patent application Ser. No. 08/234,738, filed Apr. 28, 1994, now abandoned.

BACKGROUND OF THE INVENTION

1. Field of the Invention

This invention relates to an apparatus and process for using hydrogen peroxide vapor to sterilize articles such as medical instruments, and more particularly to the use of a non-aqueous source of hydrogen peroxide vapor for such a process. The invention also provides a vapor-phase process for synthesizing organic and inorganic non-aqueous hydrogen peroxide complexes.

2. Description of the Related Art

Medical instruments have traditionally been sterilized using either heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long. In addition, both formaldehyde and ethylene oxide require the presence of a substantial amount of moisture in the system. Thus, devices to be sterilized must be humidified before the chemical is introduced or the chemical and moisture must be introduced simultaneously. Moisture plays a role in sterilization with a variety of other chemicals in the gas or vapor state, in addition to ethylene oxide and formaldehyde, as shown in Table 1.

TABLE 1

| Chemical | Relative Humidity Requirements for Optimal Efficacy | Literature Reference |
| --- | --- | --- |
| Ethylene oxide | 25–50% | 1 |
| Propylene oxide | 25–50% | 1 |
| Ozone | 75–90% | 2 |
| Formaldehyde | >75% | 1 |
| Glutaraldehyde | 80–90% | 3 |
| Chlorine dioxide | 60–80% | 4 |
| Methyl bromide | 40–70% | 1 |
| β-Propiolactone | >75% | 1 |
| Peracetic acid | 40–80% | 5 |

1. Bruch, C. W. Gaseous Sterilization, Ann. Rev. Microbiology 15:245–262 (1961).
2. Janssen, D. W. and Schneider, P. M. Overview of Ethylene Oxide Alternative Sterilization Technologies, Zentralsterilisation 1:16–32 (1993).
3. Bovallius, A. and Anas, P. Surface-Decontaiminating Action of Glutaraldehyde in the Gas-Aerosol Phase. Applied and Environmental Microbiology, 129–134 (Aug. 1977).
4. Knapp, J. E. et al. Chlorine Dioxide As a Gaseous Sterilant, Medical Device & Diagnostic Industry, 48–51 (Sept. 1986).
5. Portner, D. M. and Hoffman, R. K. Sporicidal Effect of Peracetic Acid Vapor, Applied Microbiology 16: 1782–1785 (1968).

Sterilization using hydrogen peroxide vapor has been shown to have some advantages over other chemical sterilization processes (see, e.g., U.S. Pat. Nos. 4,169,123 and 4,169,124), and the combination of hydrogen peroxide with a plasma provides additional advantages, as disclosed in U.S. Pat. 4,643,876, issued Feb. 17, 1987 to Jacobs et al. In these disclosures the hydrogen peroxide vapor is generated from an aqueous solution of hydrogen peroxide, which ensures that there is moisture present in the system. These disclosures, together with those summarized in Table 1, teach that moisture is required for hydrogen peroxide in the vapor phase to be effective or to exhibit its maximum sporicidal activity. However, using aqueous solutions of hydrogen peroxide to generate hydrogen peroxide vapor for sterilization causes problems. At higher pressures, such as atmospheric pressure, excess water in the system can cause condensation. Thus, one must reduce the relative humidity in a sterilization enclosure before introducing the aqueous hydrogen peroxide vapor.

The sterilization of articles containing diffusion-restricted areas, such as long narrow lumens, presents a special challenge for hydrogen peroxide vapor that has been generated from an aqueous solution of hydrogen peroxide, because:

1. Water has a higher vapor pressure than hydrogen peroxide and will vaporize faster than hydrogen peroxide from an aqueous solution.

2. Water has a lower molecular weight than hydrogen peroxide and will diffuse faster than hydrogen peroxide in the vapor state.

Because of this, when an aqueous solution of hydrogen peroxide is vaporized, the water reaches the items to be sterilized first and in higher concentration. The water vapor therefore becomes a barrier to the penetration of hydrogen peroxide vapor into diffusion restricted areas, such as small crevices and long narrow lumens. One cannot solve the problem by removing water from the aqueous solution and using more concentrated hydrogen peroxide, since concentrated solutions of hydrogen peroxide, i.e., greater than 65% by weight, can be hazardous, due to the oxidizing nature of the solution.

Two patents, U.S. Pat. No. 4,642,165 and U.S. Pat. No. 4,744,951 issued to Bier and Cummings et al., respectively, attempt to address this problem. Bier attempts to solve the problem by metering small increments of a hydrogen peroxide solution onto a heated surface to ensure that each increment is vaporized before the next increment is added. This helps to eliminate the difference in the vapor pressure and volatility between hydrogen peroxide and water, but it does not address the fact that water diffuses faster than hydrogen peroxide in the vapor state.

Cummings et al. describe a process for concentrating hydrogen peroxide from a relatively dilute solution of hydrogen peroxide and water and supplying the concentrated hydrogen peroxide in vapor form to a sterilization chamber. The process involves vaporizing a major portion of the water from the solution and removing the water vapor produced before injecting the concentrated hydrogen peroxide vapor into the sterilization chamber. The preferred range for the concentrated hydrogen peroxide solution is 50% to 80% by weight. This process has the disadvantage of working with solutions that are in the hazardous range; i.e., greater than 65% hydrogen peroxide, and also does not remove all of the water from the vapor state. Since water is still present in the solution, it will vaporize first, diffuse faster, and reach the items to be sterilized first. This effect will be especially pronounced in long narrow lumens.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized. In addition, water is vaporized faster and precedes the hydrogen peroxide vapor into the lumen.

Merianos discloses in U.S. Pat. No. 5,008,106, that a substantially anhydrous complex of PVP and $H_2O_2$ is useful for reducing the microbial content of surfaces. The complex, in the form of a fine white powder, is used to form antimicrobial solutions, gels, ointments, etc. It can also be applied to gauze, cotton swabs, sponges and the like. The $H_2O_2$ is released upon contact with water present on the surfaces containing the microbes. Thus, this method too requires the presence of moisture to effect sterilization.

Nikolskaya et al. disclose in U.S.S.R. patent document No. SU 1681860 that surfaces can be decontaminated, although not necessarily sterilized, using ammonium fluoride peroxohydrate ($NH_4F.H_2O_2$). However, this inorganic peroxide complex provides decontamination only within the very narrow temperature range of 70°–86° C. Even within this range, decontamination times were quite long, requiring at least two hours. Additionally, it is known that ammonium fluoride decomposes to ammonia and hydrofluoric acid at temperatures above 40° C. Due to its toxicity and reactivity, hydrofluoric acid is undesirable in most sterilization systems. Moreover, the Nikolskaya et al. reference discloses that despite the release of 90% of its hydrogen peroxide at 60° C., $NH_4F.H_2O_2$ is ineffective at decontamination of surfaces at this temperature. Thus, it appears that a factor other than hydrogen peroxide is responsible for the decontamination noted.

Hydrogen peroxide is capable of forming complexes with both organic and inorganic compounds. The binding in these complexes is attributed to hydrogen bonding between electron rich functional groups in the complexing compound and the peroxide hydrogen. The complexes have been used in commercial and industrial applications such as bleaching agents, disinfectants, sterilizing agents, oxidizing reagents in organic synthesis, and catalysts for free-radical-induced polymerization reactions.

Generally, these types of compounds have been prepared by the crystallization of the complex from an aqueous solution. For example, urea hydrogen peroxide complex was prepared by Lu, Hughes, and Giguere (*J. Amer. Chem. Soc.* 63(1):1507–1513 (1941)) in the liquid phase by adding a solution of urea to a solution of hydrogen peroxide and allowing the complex to crystallize under the proper conditions. Gates et al. (U.S. Pat. No. 2,986,448) prepared sodium carbonate hydrogen peroxide complex by treating a saturated aqueous solution of $Na_2CO_3$ with a solution of 50 to 90% $H_2O_2$ in a closed cyclic system at 0° to 5° C. for 4 to 12 hours. More recently, Hall et al. (U.S. Pat. No. 3,870,783) prepared sodium carbonate hydrogen peroxide complex by reacting aqueous solutions of hydrogen peroxide and sodium carbonate in a batch or continuous crystallizer. The crystals are separated by filtration or centrifugation and the liquors used to produce more sodium carbonate solution. These methods work well for peroxide complexes that form stable, crystalline free-flowing products from aqueous solution.

Shiraeff (U.S. Pat. Nos. 3,376,110 and 3,480,557) disclosed the preparation of a complex of hydrogen peroxide with a polymeric N-vinylheterocyclic compound (PVP) from aqueous solution. The resultant complexes contained variable amounts of hydrogen peroxide and substantial amounts of water. Merianos disclosed in U.S. Pat. No. 5,008,093 that free-flowing, stable, substantially anhydrous complexes of PVP and $H_2O_2$ could be obtained by reacting a suspension of PVP and a solution of $H_2O_2$ in an anhydrous organic solvent like ethyl acetate. More recently, Biss (U.S. Pat. No. 5,077,047) described a commercial process for producing the PVP-hydrogen peroxide product by adding finely divided droplets of a 30% to 80% by weight aqueous solution of hydrogen peroxide to a fluidized bed of PVP maintained at a temperature of ambient to 60° C. The resultant product was found to be a stable, substantially anhydrous, free flowing powder with a hydrogen peroxide concentration of 15 to 24%.

Moschner, et al. (U.S. Pat. No. 5,030,380) prepared a solid polymeric electrolytic complex with hydrogen peroxide by first forming a complex in aqueous solution and then drying the reaction product under vacuum or by spray drying at a low enough temperature to avoid thermal degradation of the product.

All these prior art methods of preparing hydrogen peroxide complexes use solutions of hydrogen peroxide. Either the complex is formed in a solution containing hydrogen peroxide or droplets of a hydrogen peroxide solution are sprayed onto a fluidized bed of the reactant material.

Vapor phase and gas phase reactions are well known synthesis methods. For example, Roetheli (U.S. Pat. No. 2,812,244) disclosed a solid-gas process for dehydrogenation, thermal cracking, and demethanation. Fujimoto et al. (*Journal of Catalysis*, 133:370–382 (1992)) described a vapor-phase carbonylation of methanol. Zellers et al. (*Analytical Chemistry*, 62:1222–1227 (1990)) discussed the reaction of styrene vapor with a square-plannar organoplatinum complex. These prior art vapor- and gas-phase reactions, however, were not used to form hydrogen peroxide complexes.

SUMMARY OF THE INVENTION

One aspect of the present invention relates to an apparatus for hydrogen peroxide sterilization of an article. The apparatus includes a container for holding the article to be sterilized, and a source of hydrogen peroxide vapor located within the container. The source includes a substantially non-aqueous organic hydrogen peroxide complex and is configured so that the vapor can contact the article to effect sterilization. In one embodiment, the container can include a breathable barrier. The complex used can be any of a variety of organic hydrogen peroxide complexes, such as a urea-peroxide complex, a polyvinylpyrrolidone-peroxide complex, a nylon 6-peroxide complex or a 1,3 dimethylurea-peroxide complex. In certain embodiments, the complex is unstable under vacuum, such as a glycine anhydride-peroxide complex. The apparatus can also include a heater located within the container, whereby the complex is placed on the heater and heated to facilitate the release of the vapor from the complex. The apparatus in certain embodiments includes an enclosure disposed outside of the container in which the complex is located, and an inlet providing fluid communication between the container and the enclosure, such that vapor released from the complex travels along the inlet and into the container to effect sterilization. In other certain embodiments, the apparatus includes a closeable valve disposed in the inlet such that when the valve is closed, the enclosure is isolated from the container. The apparatus can also include a vacuum pump in fluid communication with the container for evacuating the container. A vacuum pump in fluid communication with the container and the enclosure can also be included, along with a closeable valve disposed between the pump and the container, and between the pump and the enclosure, and between the enclosure and the container, such that the enclosure and the container can be evacuated independently or simultaneously. An electrode inside the container for generating a plasma around the article can also be included. In a preferred embodiment, the complex is in a solid phase. The apparatus can include a heater configured to heat said complex.

Another aspect of the present invention relates to a method for hydrogen peroxide vapor sterilization of an article. This method includes the steps of placing the article into a container, and contacting the article with a hydrogen peroxide vapor released from a substantially non-aqueous organic hydrogen peroxide complex to contact and sterilize the article. In one preferred embodiment, the vapor is released from a complex having no more than about 10% water. The complex can be heated to facilitate the release of the vapor from the complex. Optionally, pressure pulsing can be used to enhance sterilization. In some embodiments, the container is evacuated before introducing the vapor into the container. The method can also include the step of generating a plasma in the container after introducing the vapor into the container.

In still another aspect of the present invention, there is provided a method for hydrogen peroxide plasma sterilization of an article. This method involves placing the article within a container, contacting the article with a hydrogen peroxide vapor released from a substantially non-aqueous organic hydrogen peroxide complex to contact the article, generating a plasma within the container to surround the article, and maintaining the article in the plasma for a time sufficient to effect sterilization of the article and/or to remove residual hydrogen peroxide from the article. In one embodiment, the peroxide treatment occurs in one chamber and the plasma treatment in another.

Still one more aspect of the present invention also relates to a method for hydrogen peroxide plasma sterilization of an article. This method includes placing the article within a container, contacting the article with a hydrogen peroxide vapor released from a substantially non-aqueous organic hydrogen peroxide complex to contact the article, generating a plasma at a site that is spaced apart from the article, flowing the plasma to the container that contains the article, and maintaining the article in the plasma for a time sufficient to effect sterilization of the article and/or to remove residual hydrogen peroxide from the article. The plasma treatment can be either in the same chamber or a different chamber than the chamber in which the peroxide treatment occurs.

An additional aspect of the invention relates to a method for hydrogen peroxide sterilization of an article which includes placing the article in a enclosure containing a substantially non-aqueous hydrogen peroxide complex, sealing the enclosure, and allowing the enclosure to stand at about atmospheric pressure and at a temperature below about 70° C., more preferably below about 40° C., for a time sufficient to release substantially non-aqueous hydrogen peroxide vapor from the complex, thereby effecting sterilization of the article. The enclosure can be allowed to stand at a pressure less than atmospheric pressure and/or heated to a temperature greater than 23° C. to facilitate release of the vapor. The enclosure can be a pouch, a container, a chamber or a room. The hydrogen peroxide complex can be in the form of a powder or of a tablet. The sealing step can comprise sealing the enclosure with a gas permeable material, such as TYVEK™, CSR wrap, or paper.

A further aspect of the invention relates to a sealed enclosure containing a sterile product and a substantially non-aqueous hydrogen peroxide complex capable of releasing hydrogen peroxide vapor.

A still further aspect of the invention relates to a method for hydrogen peroxide sterilization of an article having an exterior and a narrow lumen therein. This method involves connecting a vessel containing a substantially non-aqueous hydrogen peroxide complex to the lumen of the article, placing the article within a container, evacuating the container, and contacting the lumen of the article with hydrogen peroxide vapor released from the substantially non-aqueous hydrogen peroxide complex at a temperature less than about 70° C. In a preferred embodiment, the method can also include contacting the exterior of the article with a second source of sterilant, such as one that releases hydrogen peroxide vapor. This hydrogen peroxide vapor from the second source of sterilant can be released from a second substantially non-aqueous hydrogen peroxide complex. In this embodiment, the second substantially non-aqueous hydrogen peroxide complex can be the same or different complex as the hydrogen peroxide complex referred to in the connecting step. The method can also include generating a plasma within the container to surround the article and maintaining the article in the plasma for a time sufficient to effect sterilization of the article. Further, the method can include generating a plasma within the container to surround the article and maintaining the article in the plasma for a time sufficient to remove residual hydrogen peroxide from the article.

Yet a further aspect of the present invention relates to a process for preparing a substantially non-aqueous hydrogen peroxide complex. This process includes the steps of (a) evacuating a chamber that contains a composition, and (b) introducing hydrogen peroxide vapor into the chamber, whereby the hydrogen peroxide vapor reacts with the composition to form the complex. The composition can be an alcohol, an ether, a ketone, an acid, an amino acid, an ester, an organic salt, an amine, an amide, urea, biuret, a polyamide, a polyurethane, an alkali metal carbonate, a hydroxide, or tetrasodium pyrophosphate. Some particularly preferred compositions include poly(vinyl alcohol), poly (vinyl methyl ether), poly(vinyl methyl ketone), poly(acrylic acid), glycine, L-histidine, poly(vinyl acetate), cellulose acetate, sodium alginate, cellulose sulfate (sodium salt), a histamine, glycine anhydride, propionamide, polyacrylamide, polyvinylpyrrolidone, poly(4-vinylpyridine), nylon 6, nylon 6,6 film, polyetherpolyurethane, sodium carbonate, potassium carbonate, rubidium carbonate, sodium bicarbonate, calcium hydroxide, and 1,3 dimethylurea. In some embodiments, the hydrogen peroxide vapor is substantially anhydrous.

Additional aspects of the present invention relate to a poly(vinyl alcohol)-hydrogen peroxide complex, a poly (vinyl methyl ether)-hydrogen peroxide complex, a poly (vinyl methyl ketone)-hydrogen peroxide complex, a poly (acrylic acid)-hydrogen peroxide complex, a poly(vinyl acetate) hydrogen peroxide complex, a cellulose acetate hydrogen peroxide complex, a sodium alginate hydrogen peroxide complex, a cellulose sulfate, sodium salt, hydrogen peroxide complex, a glycine-hydrogen peroxide complex, poly(4-vinylpyridine) hydrogen peroxide complex, a histamine hydrogen peroxide complex, a propionamide hydrogen peroxide complex, a 1,3-dimethylurea hydrogen peroxide complex, a biuret hydrogen peroxide complex, a polyacrylamide hydrogen peroxide complex, a nylon 6 hydrogen peroxide complex, a nylon 6,6 film hydrogen peroxide complex, a polyetherpolyurethane hydrogen peroxide complex, and a rubidium carbonate hydrogen peroxide complex.

Another aspect of the invention relates to a method for hydrogen peroxide vapor sterilization of an article in which the article is placed into a container, and the article is then contacted with a hydrogen peroxide vapor to contact and sterilize the article. In this aspect of the invention, the vapor is released from a substantially non-aqueous hydrogen peroxide complex which does not decompose to release a hydrohalic acid. A hydrohalic acid is defined herein as an acid composed of a hydrogen atom and a halogen atom, such as HCl, HF, HBr, etc.

BRIEF DESCRIPTION OF THE DRAWINGS

FIG. 4 is a graph depicting the release of hydrogen peroxide vapor from a vacuum unstable non-aqueous hydrogen peroxide complex.

DETAILED DESCRIPTION OF THE INVENTION

Figure 1:
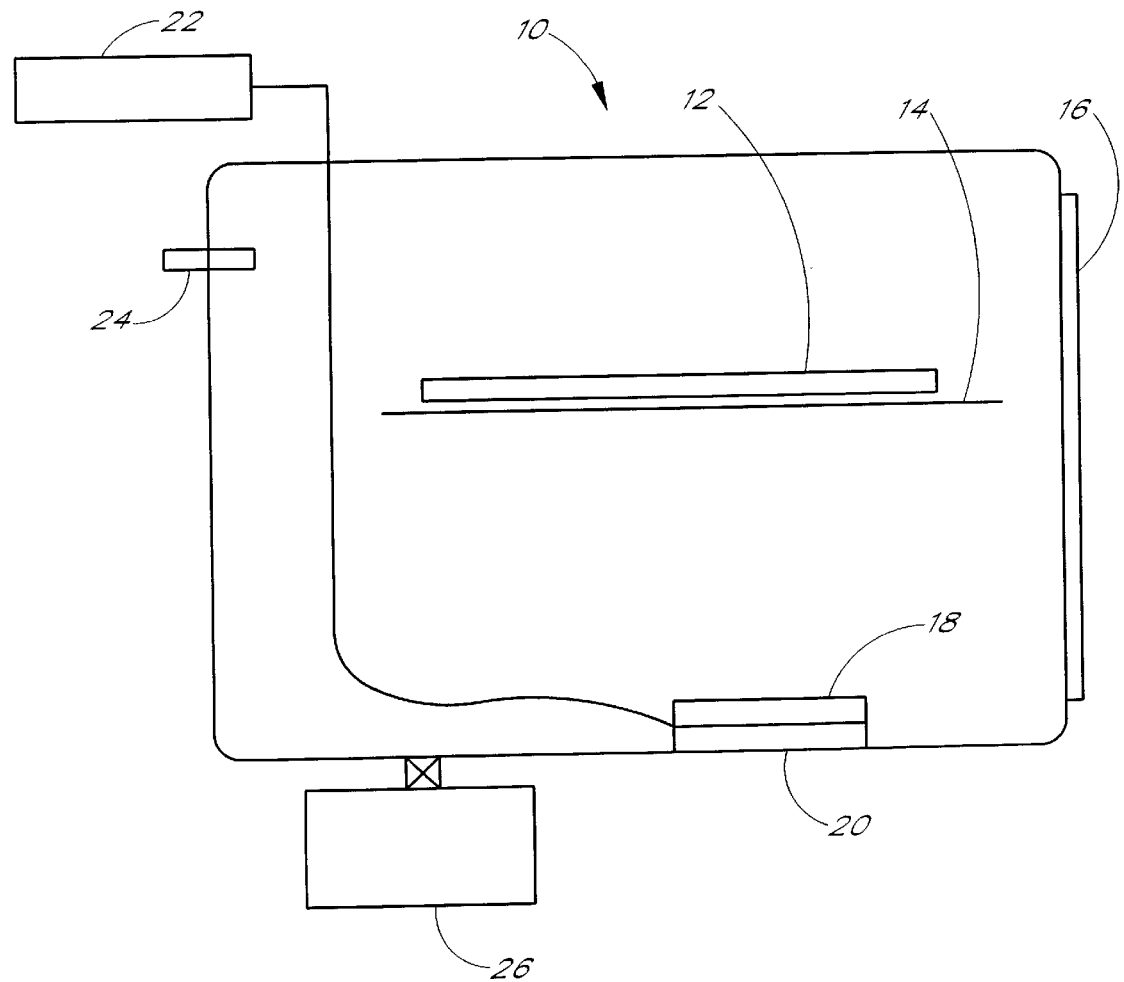
FIG. 1 is a schematic of a vapor sterilization apparatus of the present invention.

Hydrogen peroxide sterilizers that have been used in the past invariably used an aqueous solution of hydrogen peroxide as their source of sterilant. These sterilizers have disadvantages caused by the presence of water in the system. At higher pressure, such as atmospheric pressure, the excess water in the system can cause condensation. This requires that an extra step be performed to reduce the relative humidity of the atmosphere in an enclosure to be sterilized to an acceptable level before the aqueous hydrogen peroxide vapor is introduced. These sterilizers also have drawbacks caused by the facts that water, having a higher vapor pressure, vaporizes more quickly than hydrogen peroxide from an aqueous solution; and water, having a lower molecular weight, diffuses faster than hydrogen peroxide. When a medical device or the like is enclosed in a sterilizer, the initial sterilant that reaches the device from the hydrogen peroxide source is diluted in comparison to the concentration of the source. The dilute sterilant can be a barrier to sterilant that arrives later, particularly if the device being sterilized is an article, such as an endoscope, that has narrow lumens. Using a concentrated solution of hydrogen peroxide as the source in an attempt to overcome these drawbacks is unsatisfactory, because such solutions are hazardous.

In the present invention, the shortcomings of hydrogen peroxide sterilizers of the prior art are overcome by using a substantially non-aqueous (i.e., substantially anhydrous) source of hydrogen peroxide which releases a substantially non-aqueous hydrogen peroxide vapor. In a preferred embodiment, the substantially non-aqueous hydrogen peroxide vapor is produced directly from a substantially non-aqueous hydrogen peroxide complex. However, the substantially non-aqueous hydrogen peroxide vapor can also be generated from an aqueous complex which is processed during vaporization to remove water, such as under vacuum.

Thus, where an aqueous hydrogen peroxide complex is used, the aqueous complex is converted to a substantially non-aqueous hydrogen peroxide complex while carrying out the process of the present invention. Preferably, the substantially non-aqueous hydrogen peroxide complexes contain less than about 20% water, more preferably no more than about 10% water, still more preferably no more than about 5% water, and most preferably no-more than about 2% water.

As is apparent from the preferred percentages of water in the substantially non-aqueous hydrogen peroxide complexes used in the present invention, as provided above, the most preferred hydrogen peroxide complex and the peroxide vapor generated therefrom are substantially water-free. Nevertheless, as is also apparent from these figures, some water can be present in the system. Some of this water may derive from the decomposition of hydrogen peroxide to form water and oxygen as byproducts and some hydrogen binding of this water to the complex can occur.

The effect of water was measured in a series of tests, with a sterilization chamber maintained at various relative humidities. Test conditions were those described in Example 1, below, with spores supported on stainless steel blades in 3 mm×50 cm stainless steel lumens. As shown in Table 2, under the test conditions, 5% relative humidity has no effect on efficacy but 10% relative humidity decreases the sterilization rate. This example shows that small amounts of moisture can be allowed in the system with the hydrogen peroxide generated from the non-aqueous peroxide complex and the presence of water in the system can be overcome by increasing the exposure time.

TABLE 2

Effects of Relative Humidity on Efficacy
SS Blades in 3 mm × 50 cm SS Lumens

| | Sterility Results (Positive/Samples) | | |
|---|---|---|---|
| Diffusion Time | 1% RH | 5% RH | 10% RH |
| 5 | 0/3 | 0/3 | 3/3 |
| 10 | 0/3 | 0/3 | 2/3 |
| 15 | 0/3 | 0/3 | 0/3 |
| 30 | 0/3 | 0/3 | 0/3 |

A primary criterion for the composition of the hydrogen peroxide source is the relationship between its stability and hydrogen peroxide evaporation rate as a function of temperature and pressure. Depending on the parameters of the sterilization process—e.g. pressure, temperature, etc.—a higher or lower peroxide evaporation rate may be preferred, and heating the peroxide source may or may not be required. The need for heating of the peroxide complex depends on the vapor pressure of the complex. Some peroxide complexes have a sufficiently high vapor pressure that a significant amount of hydrogen peroxide vapor can be released without heating the complex. In general, heating the complex increases the vapor pressure of hydrogen peroxide and accelerates the release of peroxide from the complex.

To provide a desirably high evaporation rate, the source should preferably have a large surface area. Thus the source may be a fine powder or a coating on a material that has a large surface area. Of course, safety, availability, and cost of the material are also important criteria. The release of hydrogen peroxide from hydrogen peroxide complexes with urea, polyvinylpyrrolidone, nylon-6, glycine anhydride, and 1,3 dimethyl urea were evaluated. The complexes of hydrogen peroxide with urea, polyvinylpyrrolidone, nylon-6, and glycine anhydride are solids. The 1,3 dimethyl urea peroxide complex is a liquid. The glycine anhydride hydrogen peroxide complex is a less stable complex under reduced pressure than the other complexes evaluated, and under vacuum conditions, most of the hydrogen peroxide can be released from the complex without the need for additional heating.

Urea hydrogen peroxide complex is available in tablet form from Fluka Chemical Corp., Ronkonkoma, N.Y. and in powder form from Aldrich Chemical Co., Milwaukee, Wis. This complex is also known as urea peroxide, hydrogen peroxide urea complex, peroxide urea, peroxide urea adduct, urea peroxide adduct, percarbamide, carbamide perhydrate, and carbamide peroxide. As used herein, the term "urea peroxide" encompasses all of the foregoing terms.

The polyvinylpyrrolidone-hydrogen peroxide complex (PVP-$H_2O_2$) can be prepared by the method disclosed in International Application Pub. No. WO 92/17158. Alternatively, the complexes with PVP, with nylon-6, with 1,3 dimethylurea and with glycine anhydride, as well as with other organic and inorganic compounds can be prepared by the method disclosed in detail below.

Achieving suitable evaporation rates of anhydrous peroxide vapor from the source may be facilitated by elevated temperatures and/or reduced pressure. Thus, a heater for the peroxide source and/or a vacuum pump to evacuate the sterilization chamber are preferably a part of the sterilizer. Preferably, the source is covered with a layer of gas permeable material, such as TYVEK™ nonwoven polyethylene fabric, nonwoven polypropylene such as SPUNGUARD™, or similar material, which permits the peroxide vapor to pass but not the peroxide complexing material. Perforated aluminum or other suitable perforated material could also be used as a cover.

Figure 3A:
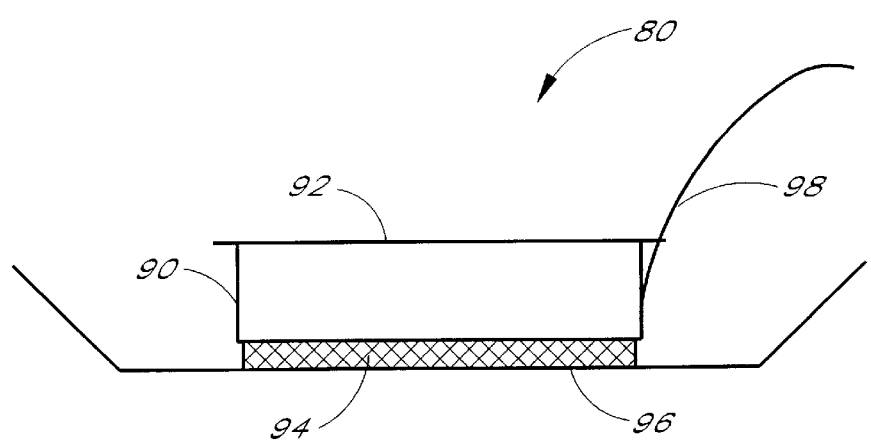
FIG. 3A is a schematic of a device which can be used for heating peroxide complexes.

FIG. 3A shows a device 80 that can be used to measure release of hydrogen peroxide from hydrogen peroxide complexes under various temperature conditions. In this device, an aluminum pan 90 is covered with a gas permeable layer 92, such as a layer of medical grade TYVEK. The pan 90 is placed on top of a heating pad 94 which is placed in a pyrex pan 96. A thermocouple thermometer 98 is placed on the outside of the pan 90 approximately 1 cm from the bottom thereof.

Figure 3B:
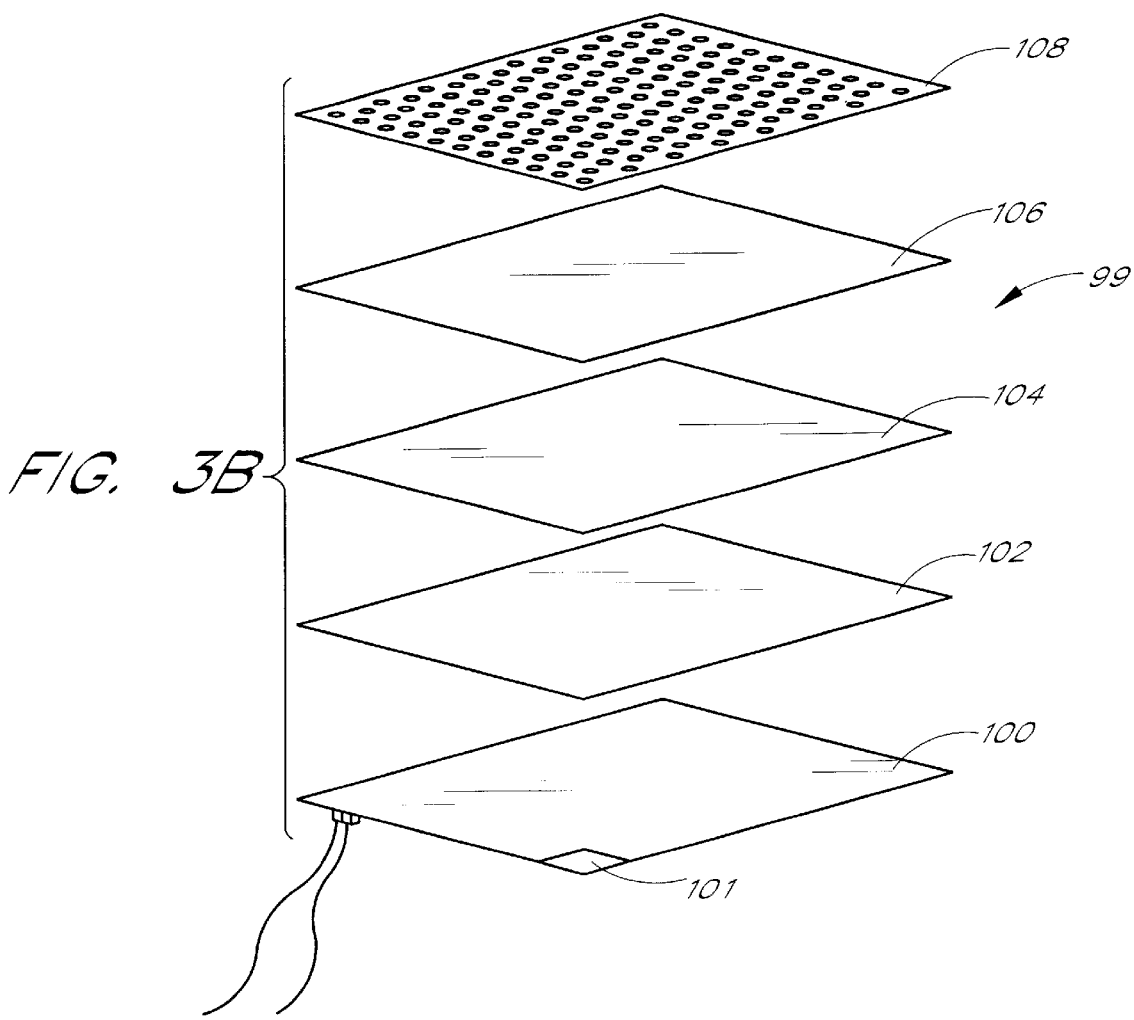
FIG. 3B is a schematic of a preferred container for holding the peroxide source for sterilization according to the present invention.

A preferred container 99 for holding the peroxide source is illustrated in FIG. 3B. The container 99 comprises a metal plate 100, e.g. an aluminum plate, with an optional attached heater used to heat the solid peroxide complex. A temperature monitor 101, such as a thermometer, can be placed on the plate 100 to monitor the temperature. The peroxide complex is placed directly on the plate 100. Alternatively, in order to provide even heating of all the peroxide complex, the peroxide complex can be placed between one or more aluminum screens 102, 104 placed on top of the plate 100. The aluminum screens 102, 104 provide greater surface area and even heating of the complex when larger amounts of peroxide complex are being used. The peroxide complex, or the screen or screens 102, 104, are then covered with a gas permeable layer 106, such as a layer of medical grade TYVEK™ or SPUNGUARD™, so that the hydrogen peroxide released from the complex passes through the covering 106 before diffusing into the rest of the chamber. A perforated aluminum plate 108 is optionally placed on top of the TYVEK™ or SPUNGUARD™ layer 106 to provide pressure to keep the complex in contact with the heated plate 100 and to ensure even heating of the peroxide complex.

The device just described provides even heating of the complex, which results in an increased amount of hydrogen peroxide vapor being released from the peroxide complex.

FIG. 1 depicts a schematic of a hydrogen peroxide vapor sterilization apparatus of the present invention. Chamber 10 holds an article 12 which is to be sterilized and which, for convenience, is placed on shelf 14. Door 16 provides access to the interior of chamber 10. A non-aqueous source of hydrogen peroxide 18 is depicted on optional heater 20, which is controlled by temperature controller 22. The peroxide concentration can be monitored by optional monitor 24. If desired, chamber 10 can be evacuated using pump 26; however, sterilization can also be accomplished at atmospheric pressure.

The container that holds the articles to be sterilized can be a conventional sterilization chamber, which is evacuated, or it can be a container (or a room) at atmospheric pressure.

The time required to sterilize the articles depends on the nature, number and packaging of the articles and their placement in the chamber. Alternatively, it may be the chamber itself (or an entire room) that is being sterilized. In any case, optimum sterilization times can be determined empirically.

The use of pressure pulsing to enhance the penetration and antimicrobial activity of sterilant gases, which is well known in the sterilization art, can also be applied to the non-aqueous hydrogen peroxide process. As described in additional detail hereinbelow, plasma can also be used to further enhance activity.

At the conclusion of the sterilization process excess hydrogen peroxide can be removed from devices that have an affinity for peroxide by exchanging the air in contact with the devices. This can be accomplished by flowing warm air over the devices for an extended time or by evacuating the chamber.

Articles that have previously been sterilized by exposure to hydrogen peroxide vapor may also be exposed to the plasma to remove residual hydrogen peroxide that may remain on the articles. Since the hydrogen peroxide is decomposed into non-toxic products during the plasma treatment, the sterilized articles may be used without the need for any additional steps.

It may be desirable to isolate the peroxide source from the sterilizer after the peroxide vapor is released to avoid reabsorption of the vapor or, when a plasma is used, to avoid exposing the source to the plasma. Isolation is also advantageous when the complex used is not stable under vacuum. Isolation can be accomplished using valves or other isolating devices well known in the art.

Figure 2:
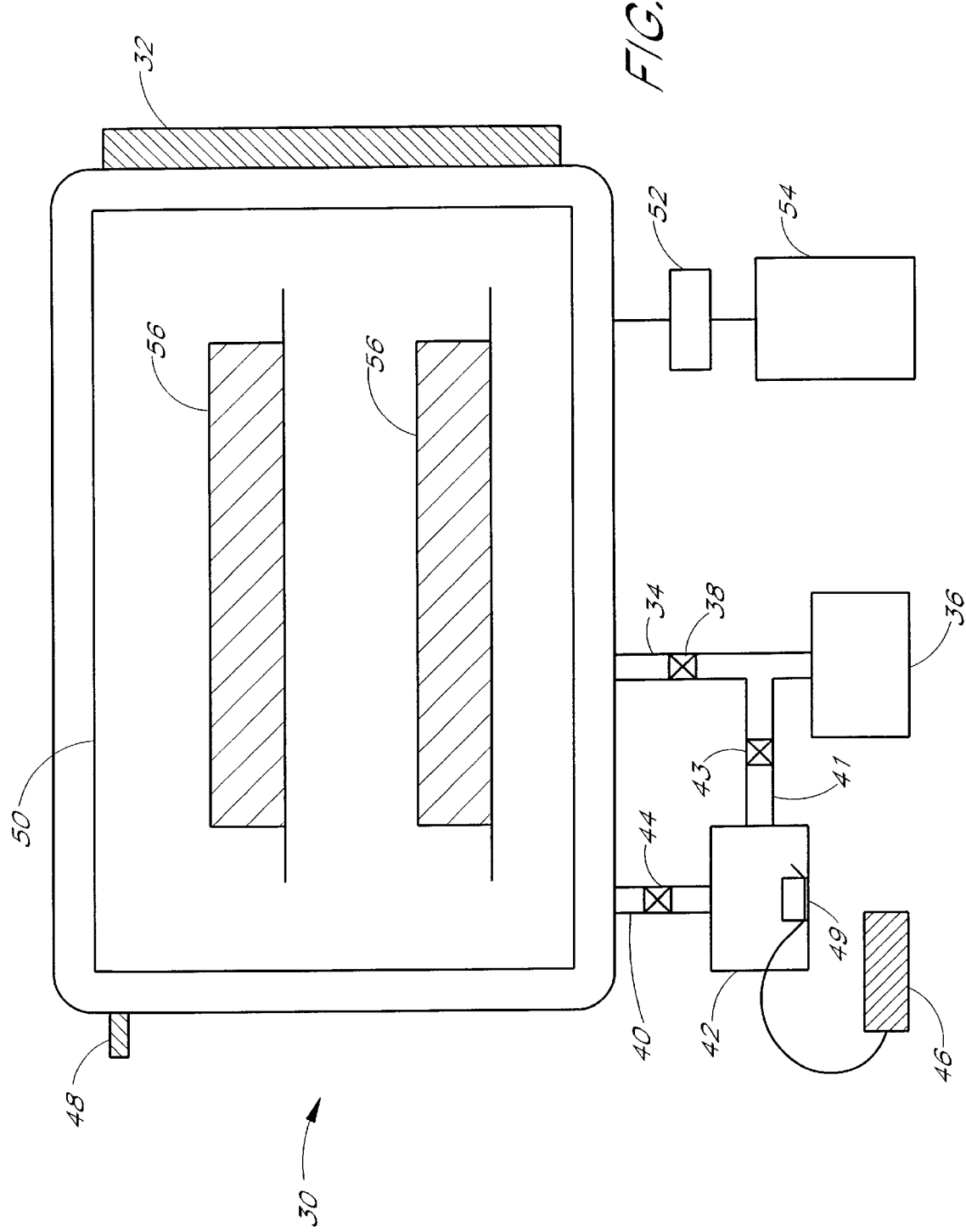
FIG. 2 is a schematic of a vapor sterilization apparatus of the present invention which includes an electrode which is optionally used to generate plasma.

FIG. 2 depicts a schematic of a hydrogen peroxide plasma sterilization system of the present invention. Sterilization can be achieved with or without the use of plasma. The plasma can be used to enhance the sporicidal activity of the peroxide vapor, and/or to remove any residual hydrogen peroxide remaining on the sterilized articles.

Sterilization is carried out in chamber 30, which includes a door or opening 32 through which articles to be sterilized can be introduced. The chamber 30 includes an outlet 34 to a vacuum pump 36, through which the chamber can be evacuated. The outlet 34 contains a valve 38 to isolate the chamber from the vacuum pump 36. The chamber 30 also includes an inlet 40 attached to an enclosure 42 that contains the hydrogen peroxide complex. Inlet 40 contains a valve 44 that allows enclosure 42 to be isolated from the chamber. The sterilization system also contains an inlet 41 which connects the enclosure 42 and the vacuum pump 36, which contains a valve 43. This system allows the simultaneous evacuation of both enclosure 42 and chamber 30, or the independent evacuation of either enclosure 42 or chamber 30. Evacuation is controlled by the opening and closing of the valves 38, 44, and 43. As will be apparent to one having ordinary skill in the art, two pumps, one for each chamber, could also be employed in this system.

The enclosure 42 contains an optional heater 49 attached to a temperature controller 46 to control the temperature of the hydrogen peroxide complex. The hydrogen peroxide complex concentration in the vapor state can be monitored by an optional peroxide monitor 48. The interior of the chamber contains a radio frequency (RF) electrode 50, to which is attached a matching network 52 and an RF power supply 54. A convenient form for the electrode is a perforated cylinder, surrounding the samples and open at both end. The general operation of the present process is as follows:

1. The articles 56 to be sterilized are placed in the chamber 30.

2. The chamber 30 may be at atmospheric pressure or, alternatively, may be evacuated to facilitate penetration of the hydrogen peroxide. Evacuation is accomplished by opening valve 38 and turning on vacuum pump 36. Alternatively, both the chamber 30 and the enclosure 42 may be evacuated by opening valves 38 and 44, and/or 43.

3. The valves 38 and 43 are closed to isolate the vacuum pump 36 from the chamber 30 and enclosure 42, and the valve 44 is opened. Hydrogen peroxide vapor is delivered into chamber 30 from the hydrogen peroxide source, which may be heated to facilitate the release of the hydrogen peroxide vapor. Optionally, air or an inert gas may also be added.

4. The articles 56 to be sterilized are either treated with peroxide vapor until sterilized or pretreated with peroxide vapor in the chamber 30 before plasma with sufficient power to sterilize is generated. If necessary, chamber 30 may be evacuated at this time to facilitate generation of the plasma. The duration of the pre-plasma holding period depends on the type of package used, the nature and number of items to be sterilized, and the placement of the items in the chamber. Optimum times can be determined empirically.

5. The articles 56 are subjected to a plasma by applying power from the RF power supply 54 to the RF electrode 50. The RF energy used to generate the plasma may be pulsed or continuous. The articles 56 remain in the plasma for a period to effect complete sterilization and/or to remove residual hydrogen peroxide. In certain embodiments, 5 to 30 minutes of plasma is used. However, optimum times can be determined empirically.

When used in the present specification and claims, the term "plasma" is intended to include any portion of the gas or vapor that contains electrons, ions, free radicals, dissociated and/or excited atoms or molecules produced as a result of an applied electric field, including any accompanying radiation that might be produced. The applied field may cover a broad frequency range; however, a radio frequency or microwaves are commonly used.

The non-aqueous hydrogen peroxide delivery system disclosed in the present invention can also be used with plasmas generated by the method disclosed in the previously mentioned U.S. Pat. No. 4,643,876. Alternatively, it may be used with plasmas described in U.S. Pat. Nos. 5,115,166 or 5,087,418, in which the article to be sterilized is located in a chamber that is separated from the plasma source.

The device just described is particularly advantageous when using peroxide complexes that are not stable under vacuum. There are at least two possible methods that can be used to minimize the loss of hydrogen peroxide during the vacuum stage. First, the small chamber can be evacuated independently. Second, if a small enough chamber is used, there is no need to evacuate the small chamber at all.

One such unstable non-aqueous peroxide complex is glycine anhydride-peroxide. This compound releases hydrogen peroxide vapor when placed under vacuum. FIG. 4 is a graph illustrating the release of hydrogen peroxide vapor from glycine anhydride-peroxide complex under vacuum. The procedure used to release the hydrogen peroxide from the glycine anhydride complex is as follows: (1) The main chamber 30 was evacuated with valves 43 and 44 closed. (2) The chamber containing the hydrogen peroxide complex 42 was evacuated with valves 38 and 44 closed and valve 43 open. (3) Valve 43 was closed and valve 44 was opened and hydrogen peroxide vapor was allowed to diffuse into chamber 30.

As shown by the graph, hydrogen peroxide vapor is released from the complex as the pressure is reduced, even without additional heating. As illustrated in FIG. 4, release of peroxide vapor is significantly increased by heating the complex to a higher temperature. Thus, even unstable peroxide complexes are useful in the sterilization method of the present invention.

The present invention provides at least four advantages over earlier hydrogen peroxide sterilization systems:

1. The use of concentrated, potentially hazardous hydrogen peroxide solutions is circumvented.

2. The need to reduce beforehand the relative humidity of areas to be sterilized in order to prevent condensation is eliminated.

3. Water is substantially eliminated from the system, so that there is little competition between water and hydrogen peroxide for diffusion into long narrow lumens.

4. The need to attach a special vessel to deliver sterilant gases into long narrow lumens can often be eliminated.

That sterilization can be effected using hydrogen peroxide vapor in the substantial absence of moisture is one of the surprising discoveries of the present invention. The prior art teaches that the presence of water is required to achieve sterilization in chemical gas or vapor state sterilization processes. Advantageously, the present invention substantially eliminates water from the system, which results in faster, more efficient and effective sterilization.

The sterilization efficacy of various non-aqueous hydrogen peroxide complexes was determined as described below in Examples 1–4.

EXAMPLE 1

Efficacy data was obtained with hydrogen peroxide vapor released from substantially anhydrous urea peroxide complex using *Bacillus subtilis* var. (*niger*) spores in metal and TEFLON™ plastic lumens as the biological challenge.

A. Test Procedures

1. Equipment

Four grams of crushed hydrogen peroxide urea adduct tablet (Fluka Chemical Corp, Ronkonkoma, N.Y.) were placed in an aluminum pan 90, as described in FIG. 3A. The top of the pan 90 was covered with medical grade TYVEK™ 92 (a breathable spunbond polyethylene fabric) so that any hydrogen peroxide released from the complex would need to pass through the TYVEK™ covering before diffusing into the rest of the chamber. The aluminum pan 90 was placed on a heating pad 94 in a pyrex dish 96 located in the bottom of an aluminum sterilization chamber (see FIG. 1). The sterilization chamber, which had an approximate volume of 173 liters, also contained:

A hydrogen peroxide monitor for measuring hydrogen peroxide concentration in the vapor phase.

A temperature controller for controlling the temperature of the heating pad.

An injection port through which liquid hydrogen peroxide could be injected into the chamber.

A metal shelf on which a plastic tray containing lumen devices were placed for testing.

Electrical resistance heaters on the exterior of the chamber walls, which maintained the chamber temperature at 45° C. during the efficacy testings.

2. Biological Challenge and Test

To evaluate the efficacy of the non-aqueous peroxide delivery system, a biological challenge consisting of 1.04× $10^6$ B. subtilis var. (niger) spores on a stainless steel scalpel blade was placed equally distant from each end of the stainless steel lumens of dimensions 3 mm ID×40 cm length, 3 mm ID×50 cm length, and 1 mm ID×50 cm length. These ID's and lengths are typical for metal lumens used in medical devices. The compartment in the middle of each lumen that contained the biological test piece had the dimensions 13 mm ID×7.6 cm length. In the biological testing with metal lumens, a total of 9 lumens were evaluated per test. These included 3 lumens from each of the 3 different sets of ID's and lengths available.

Similar tests were conducted with a biological challenge consisting of 4.1×$10^5$ B. subtilis var. (niger) spores on a paper strip (6 mm×4 mm Whatman #1 chromatography paper) located equally distant from the ends of TEFLON™ lumens of dimensions 1 mm ID×1 meter length, 1 mm ID×2 meter length, 1 mm ID×3 meter length, and 1 mm ID×4 meter length. The center compartment of these lumens that contained the biological test piece had the dimensions 15 mm ID×7.6 cm length. In the biological testing with TEFLON™ lumens, a of 12 lumens were evaluated per test, 3 lumens from each of the 4 different lengths available.

The lumens containing the biological test samples were placed in a plastic tray that was then placed on the shelf in the sterilization chamber. The chamber door was then closed and the chamber evacuated to 0.2 Torr pressure with a vacuum pump. The aluminum pan containing the hydrogen peroxide urea adduct was then heated to 80° to 81° C. for a period of 5 minutes, as measured by a thermocouple thermometer placed on the side wall of the aluminum pan approximately 1 cm from the bottom of the pan. During this time the concentration of hydrogen peroxide in the chamber increased to 6 mg/L as measured by the peroxide monitor.

The biological test samples were exposed to the hydrogen peroxide vapor for periods of 5, 10, 15, 20, and 25 minutes. After exposure to the hydrogen peroxide vapor, the biological test samples were aseptically transferred into 15 mL of trypticase soy broth containing 277 units of catalase to neutralize any hydrogen peroxide residuals that may remain on the test samples. All samples were incubated for 7 days at 32° C. and observed for growth.

Comparative studies were also conducted in which a 50% aqueous solution of hydrogen peroxide was injected into the sterilization chamber and vaporized from a heated injector (a heated metal surface). The volume of hydrogen peroxide solution injected produced a vapor phase concentration of hydrogen peroxide of 6 mg/L. The test lumens and biological test samples used in these tests were identical to those used in the non-aqueous hydrogen peroxide tests. The handling of the biological test samples after exposure to the hydrogen peroxide was also identical.

B. Test Results

The results of these tests with stainless steel and TEFLON™ lumens, which are presented in Tables 3 and 4, respectively, illustrate the advantages of the non-aqueous peroxide delivery system with both metal and non-metal lumens. Total kill of the bacterial spores was achieved within 5 minutes with the non-aqueous peroxide delivery system for the smallest ID and the longest lumens evaluated. At the same time, total kill was not achieved even after 25 minutes of diffusion time with the 50% hydrogen peroxide solution.

TABLE 3

Aqueous/Non-Aqueous Efficacy Comparison
SS Blades in SS Lumens

| SOURCE OF PEROXIDE | DIFFUSION TIME (MIN) | STERILITY RESULTS (POSITIVE/SAMPLES) | | |
|---|---|---|---|---|
| | | 3 mm × 40 cm | 3 mm × 50 cm | 1 mm × 50 cm |
| 50% SOLUTION | 5 | 3/3 | 3/3 | 3/3 |
| | 10 | 0/3 | 2/3 | 3/3 |
| | 15 | 1/3 | 1/3 | 1/3 |
| | 20 | 0/3 | 0/3 | 1/3 |
| | 25 | 0/3 | 0/3 | 1/3 |
| UREA PEROXIDE | 5 | 0/3 | 0/3 | 0/3 |
| | 10 | 0/3 | 0/3 | 0/3 |
| | 15 | 0/3 | 0/3 | 0/3 |
| | 20 | 0/3 | 0/3 | 0/3 |
| | 25 | 0/3 | 0/3 | 0/3 |

TABLE 4

Aqueous/Non-Aqueous Efficacy Comparison
6 mm × 4 mm Paper strip in TEFLON ™ Lumens

| SOURCE OF PEROXIDE | DIFFUSION TIME (MIN) | STERILITY RESULTS (POSITIVE/SAMPLES) | | | |
|---|---|---|---|---|---|
| | | 1 mm × 1 m | 1 mm × 2 m | 1 mm × 3 m | 1 mm × 4 m |
| 50% SOLUTION | 5 | 3/3 | 3/3 | 3/3 | 3/3 |
| | 10 | 3/3 | 3/3 | 3/3 | 3/3 |
| | 15 | 0/3 | 1/3 | 1/3 | 2/3 |
| | 20 | 0/3 | 0/3 | 1/3 | 1/3 |
| | 25 | 0/3 | 0/3 | 0/3 | 1/3 |
| UREA PEROXIDE | 5 | 0/3 | 0/3 | 0/3 | 0/3 |
| | 10 | 0/3 | 0/3 | 0/3 | 0/3 |
| | 15 | 0/3 | 0/3 | 0/3 | 0/3 |
| | 20 | 0/3 | 0/3 | 0/3 | 0/3 |
| | 25 | 0/3 | 0/3 | 0/3 | 0/3 |

The fact that rapid sterilization can be accomplished in the absence of substantial amounts of water is surprising, in light of the fact that moisture has generally been present during chemical gas/vapor phase sterilization by various sterilants other than hydrogen peroxide. Since vapor phase hydrogen peroxide sterilization systems have used aqueous solutions of hydrogen peroxide, there has been moisture present in those systems as well.

To test the sterilization efficacy of various other peroxide complexes, the following experiments were performed.

EXAMPLE 2, 3 AND 4

The apparatus of Example 1 was used to test the efficacy of polyvinylpyrrolidone-hydrogen peroxide complex (Example 2), nylon 6-hydrogen peroxide complex (Example 3), and 1,3 dimethylurea hydrogen peroxide complex (Example 4). These compounds were synthesized according to the method disclosed below in Examples 12 and 13. Test parameters were as follows:

|  | Example | | |
|---|---|---|---|
|  | 2 | 3 | 4 |
| Chamber Temp. | 45° C. | 45° C. | 45° C. |
| Initial Pressure | 0.2 Torr | 1.0 Torr | 1.0 Torr |
| Wt. % of peroxide | 17% | 10.5% | 26.6% |
| Peroxide concentration | 6 mg/L | 6 mg/L | 6 mg/L |
| Wt. of complex used per cycle | 8 g | 18 g | 6 g |
| Temp to release peroxide | 110° C. | 110° C. | 80° C. |

In each case, spore supports were 6 mm×4 mm paper substrates in plastic lumens and stainless steel blades in stainless steel lumens. The results of this efficacy testing appear below in Table 5.

TABLE 5

Efficacy of Complexes with PVP, nylon 6, and 1,3-dimethylurea

| TYPE OF LUMEN | SIZE OF LUMENS | STERILITY RESULTS (POSITIVE/SAMPLES) With 5 Minutes Exposure | | |
|---|---|---|---|---|
|  |  | Example 2 | Example 3 | Example 4 |
| TEFLON™ | 1 mm × 1 m | 0/3 | 0/3 | 0/3 |
|  | 1 mm × 2 m | 0/3 | 0/3 | 0/3 |
|  | 1 mm × 3 m | 0/3 | 0/3 | 0/3 |
|  | 1 mm × 4 m | 0/3 | 0/3 | 0/3 |
| STAINLESS STEEL | 3 mm × 40 cm | 0/3 | 0/3 | 0/3 |
|  | 3 mm × 50 cm | 0/3 | 0/3 | 0/3 |
|  | 1 mm × 50 cm | 0/3 | 0/3 | 0/3 |

The results appearing in Table 5 show that each of the tested hydrogen peroxide complexes generate peroxide vapor which provides efficient sterilization after only five minutes exposure.

The temperature required to release the hydrogen peroxide vapor from the solid complex which is shown above is the temperature measured by a thermocouple thermometer located on the outside of the aluminum pan approximately 1 cm from the bottom of the pan. Further testing using a thermometer, such as a fluoroptic thermometer, placed on the inside bottom of the pan indicated that the temperature at the bottom of the pan was approximately 30°–35° C. higher, as described in Example 5 below. Thus, in the previous example, the temperature at the bottom of the pan was approximately 110°–115° C. when the thermocouple thermometer read 80° C., and the temperature at the bottom of the pan was approximately 140°–145° C. when the thermocouple thermometer read 110° C.

EXAMPLE 5

To determine the temperature at the bottom of the aluminum pan used to contain the solid peroxide complex, a fluoroptic thermometer was taped to the inside bottom of the aluminum pan. An Omega™ thermocouple thermometer was placed on the outside of the aluminum pan approximately 1 cm from the bottom of the pan. Three different readings of the thermometers were taken. Each time the pan was heated to the desired temperature indicated by the thermometer placed on the side of the pan, allowed to cool, and then re-heated to the desired temperature. The recorded temperatures are listed below:

| Temp. at side of pan | Temp. at bottom of pan (°C.) | | | |
|---|---|---|---|---|
|  | 1st | 2nd | 3rd | avg |
| 80° C. | 110.9 | 110.6 | 110.6 | 110.7 |
| 100° C. | 131.5 | 132.6 | 132.0 | 132.0 |

The results show that the temperature at the bottom of the aluminum pan was approximately 30°–35° C. higher than the temperature indicated by the thermocouple thermometer located at the side of the pan.

Further testing was performed to compare the efficacy data obtained using an aqueous and non-aqueous source of peroxide in an open (non-lumen) system. The experiments are described in detail below.

EXAMPLE 6

The apparatus of Example 1 was used with a biological challenge that consisted of $6.8 \times 10^5$ B. subtilis var (niger) spores on a 6 mm×4 mm strip of Whatman #1 chromatography paper packaged in a TYVEK™/MYLAR™ envelope. (TYVEK™ is a gas permeable fabric made of polyethylene. MYLAR™ is a non-gas permeable polyester material). Packaged biological challenge strips were placed in the front, middle and back of a polyphenylene oxide tray that contained a flexible fiberoptic sigmoidoscope. The tray was placed in a polyphenylene oxide container that had one port in the top and two ports in the bottom to allow for diffusion. The four-inch diameter ports were covered with a breathable polypropylene packaging material (SPUNGUARD™ Heavy Duty Sterilization Wrap, Kimberly-Clark, Dallas, Tex.) to maintain the sterility of the contents of the container after sterilization. The container was placed in the apparatus of Example 1 and the pressure in the chamber was reduced to 0.2 Torr. The aluminum pan containing 2 grams of hydrogen peroxide urea adduct (Fluka Chemical Corp.) was then heated to 80° to 81° C., as measured by a thermocouple thermometer placed on the outside of the aluminum pan approximately 1 cm from the bottom of the aluminum pan, for 5 minutes to provide 3 mg/L of hydrogen peroxide vapor in the chamber. The biological test samples were exposed to the hydrogen peroxide vapor for periods of 5 and 10 minutes. After exposure the test samples were handled in the same way as were those in Example 1.

Comparative studies were also conducted in which a 50% aqueous solution of hydrogen peroxide was injected into the sterilization chamber and vaporized from a heated injector. The volume of hydrogen peroxide solution injected produced a vapor phase concentration of 3 mg/L. The test configuration, the composition of the biological test samples, and the handling of the biological test samples after exposure were all identical to those used in the non-aqueous hydrogen peroxide tests. The results of these tests are presented in Table 6.

TABLE 6

Aqueous/Non-Aqueous Efficacy Comparison in Open System (Non-Lumen Test)

| Source of Peroxide | Diffusion Time (min) | Sterility Results (positive/samples) |
|---|---|---|
| 50% solution | 5 | 3/3 |
|  | 10 | 3/3 |
| Urea Peroxide | 5 | 1/3 |
|  | 10 | 0/3 |

The results of these tests demonstrate the greater efficacy of the non-aqueous when compared with the aqueous hydrogen peroxide process in an "open" system in which the biological sample was not placed in a lumen. Again, it was surprisingly discovered that a non-aqueous system provided superior sterilization even when diffusion of hydrogen peroxide into a long and narrow lumen is not required. This suggests that the mode of action of hydrogen peroxide is not the same for systems with and without water.

Further testing was performed to determine the efficacy a non-aqueous peroxide vapor at normal, not reduced, pressure. This testing is detailed below.

EXAMPLE 7

Efficacy tests were conducted with the hydrogen peroxide vapor released from the urea peroxide complex in an open system at atmospheric pressure. In this test the biological challenge of $1.04 \times 10^6$ B. subtilis var. (niger) spores on the stainless steel surgical blades were packaged in a TYVEK™/MYLAR™ envelope. Packaged biological challenge blades were placed on the front, middle, and back of a polyphenylene oxide tray. The tray was placed in the apparatus of Example 1 and the chamber door was closed. The aluminum pan containing 4.0 gm of urea peroxide (Fluka Chemical Corp.) was heated to 80° to 81° C., as measured by a thermocouple thermometer placed on the side of the aluminum pan approximately 1 cm from the bottom of the pan, for the duration of the test. The biological test samples were exposed to the hydrogen peroxide vapor for periods of 5, 10, 20 and 30 minutes. After exposure the test samples were handled the same way as those in Example 1. The results of these tests are presented in Table 7 and demonstrate the efficacy of the non-aqueous peroxide process in an open system at atmospheric pressure.

TABLE 7

Efficacy of non-aqueous peroxide process in open system at atmospheric pressure

| Source of Peroxide | Diffusion Time (minutes) | Sterility Results (positive/samples) |
| --- | --- | --- |
| Urea Peroxide | 5 | 3/3 |
| | 10 | 1/3 |
| | 20 | 0/3 |
| | 30 | 0/3 |

Further tests were conducted to determine the approximate amount of peroxide released from the hydrogen peroxide urea complex at various temperatures. This testing is described in Example 8.

EXAMPLE 8

Urea peroxide powder, obtained from crushing the commercially available tablets (Fluka Chemical Corp.), was placed between two aluminum screens in an apparatus according to FIG. 3B having dimensions 12.7 cm×12.7 cm. The aluminum plate was then heated and the temperature was monitored using a thermometer located near a corner of the aluminum plate. Table 8 lists the approximate percent of peroxide released at various temperatures after heating for five minutes. The data show that approximately 100% of the peroxide is released from the complex at a temperature of 140° C. Lesser percentages of peroxide are released at lower temperatures.

TABLE 8

Release of non-aqueous peroxide at various temperatures

| Heating Temperature | % Peroxide Released |
| --- | --- |
| 80° C. | ~25% |
| 100° C. | ~65% |
| 120° C. | ~80% |
| 130° C. | ~90% |
| 140° C. | ~100% |

Peroxide complexes having the ability to release hydrogen peroxide vapor at room temperature and atmospheric pressure, such as the urea peroxide complex, allows them to be effective for use in various sterilization applications. Not only can they be used in the sterilization apparatus of the present invention described above, the compounds of the present invention can also be used as part of self-sterilizing packaging materials, or applied onto supports such as gauze, sponge, cotton, and the like. The compounds allow for sterilization of sealed packages at room temperature or at elevated temperatures, and are particularly useful for the sterilization of packaged medical or surgical products.

Particular uses of the compounds of the present invention are described in the examples which follow. The peroxide complex used in the following examples was urea peroxide in the form of a table (Fluka Chemical Corp.) or in the form of a powder obtained by crushing the tablets.

EXAMPLE 9

A self-sterilizing pouch was assembled as follows: A surgical scalpel having $3.8 \times 10^5$ B. subtilis var. niger spores on its surface was placed in a sterile petri dish. The dish was placed in a larger petri dish, together with 1 gm urea peroxide complex in either tablet or powder form. The larger petri dish was then inserted into a pouch formed of TYVEK™/MYLAR™ (gas permeable, Table 9), MYLAR™/MYLAR™ (non-gas permeable, Table 10) or Paper/MYLAR™ (gas permeable, Table 10). The pouch was then sealed.

Each pouch was exposed to various temperatures for various time periods, as shown in Tables 9 and 10 below. The biological test samples were evaluated for sterilization as described in Example 1. The results are included in Tables 9 and 10, with a "+" sign indicating bacterial growth.

TABLE 9

Self-Sterilizing Pouches
With Breathable Barrier (TYVEK ™/MYLAR ™)

| Temperature | Peroxide Type | 1 hr. | 2 hr. | 3 hr. | 4 hr. |
| --- | --- | --- | --- | --- | --- |
| 23° C. | powder | + | – | – | – |
| | tablet | + | + | – | – |
| 40° C. | powder | – | – | – | – |
| | tablet | – | – | – | – |
| 60° C. | powder | – | – | – | – |
| | tablet | – | – | – | – |

Table 10 lists the efficacy data for self-sterilizing pouches with (Paper/MYLAR™) and without (MYLAR™/MYLAR™) a breathable barrier. The pouches were assembled as described above, however the peroxide vapor source was urea peroxide in powder form only.

TABLE 10

Self-Sterilizing Pouches With & Without Breathable Barrier

| Temperature | Packaging Type | 2 hr. | 4 hr. |
|---|---|---|---|
| 23° C. | MYLAR/MYLAR | – | – |
|  | Paper/MYLAR | + | – |
| 40° C. | MYLAR/MYLAR | – | – |
|  | Paper/MYLAR | – | – |
| 60° C. | MYLAR/MYLAR | – | – |
|  | Paper/MYLAR | – | – |

Results from this testing show that the urea peroxide complex of the present invention included in a pouch with and without a breathable barrier provides effective sterilization to an article inside the pouch in the absence of moisture at room temperature and atmospheric pressure after only 2 to 3 hours. At higher temperatures, sterilization is effected after only one hour.

To determine the efficacy of the sterilization system of the present invention in a closed container, the following experiment was performed.

EXAMPLE 10

A self-sterilizing container was assembled as follows: A stainless steel support having either $3.8 \times 10^5$ B. subtilis var. niger spores on its surface (Table 11) or having $9.2 \times 10^5$ B. subtilis var. niger spores on its surface (Table 12), was placed inside a small polyethylene (PE) vial having 20 holes (3/16" in size) in its surface. The vial was placed in a larger PE vial, which was covered with either an air tight cap, or a gas permeable layer of SPUNGUARD™ (CSR Wrap). Also included in the larger vial was a second PE vial, also having 20 holes (3/16" in size) in its surface. This vial contained 1 gm urea peroxide in either powder or tablet form, and was sealed in either a SPUNGUARD™ (CSR wrap) or TYVEK™ pouch.

Each container was exposed to various temperatures for various time periods, as shown in Tables 11 and 12 below. The biological test samples were evaluated for sterilization as described in Example 1. The results are included in Tables 11 and 12, with a "+" sign indicating bacterial growth.

TABLE 11

Self-Sterilizing Containers Without Breathable Window

| Temperature | Packaging Type | 2 hr. | 6 hr. |
|---|---|---|---|
| 23° C. | Unpackaged tablet | + | – |
|  | C/C* packaged tablet | + | – |
|  | C/C packaged powder | + | – |
| 40° C. | Unpackaged tablet | – | – |
|  | C/C packaged tablet | – | – |
|  | C/C packaged powder | – | – |
| 60° C. | Unpackaged tablet | – | – |
|  | C/C packaged tablet | – | – |
|  | C/C packaged powder | – | – |

*– pouch formed from CSR wrap

TABLE 12

Self-Sterilizing Containers With Breathable CSR Window

| Temperature | Packaging Type | 0.5 hr. | 1.0 hr. | 1.5 hr. | 2.0 hr. | 3.0 hr. | 4.0 hr. |
|---|---|---|---|---|---|---|---|
| 23° C. | Unpackaged tablet |  | + | + | + | – | – |
|  | Unpackaged powder |  | + | + | + | – | – |
|  | T/T* packaged tablet |  | + | + | + | + | – |
|  | T/T packaged powder |  | + | + | + | – | – |
|  | C/C** packaged tablet |  | + | + | + | – | – |
|  | C/C packaged powder |  | + | + | + | – | – |
| 40° C. | Unpackaged tablet | – | – | – | – |  |  |
|  | Unpackaged powder | – | – | – | – |  |  |
|  | T/T packaged tablet | + | – | – | – |  |  |
|  | T/T packaged powder | – | – | – | – |  |  |
|  | C/C packaged powder | – | – | – | – |  |  |
|  | C/C packaged powder | – | – | – | – |  |  |
| 60° C. | Unpackaged tablet | – | – | – | – |  |  |
|  | Unpackaged powder | – | – | – | – |  |  |
|  | T/T packaged tablet | – | – | – | – |  |  |
|  | T/T packaged powder | – | – | – | – |  |  |
|  | C/C packaged tablet | – | – | – | – |  |  |
|  | C/C packaged powder | – | – | – | – |  |  |

*– pouch formed from TYVEK™
**– pouch formed from CSR wrap

Results from this testing show that the non-aqueous urea peroxide complex included in a container with and without a breathable barrier provides effective sterilization at room temperature after only 3–4 hours. At higher temperatures, sterilization is effected after as little as one half hour.

The non-aqueous peroxide complexes which release peroxide vapor have been found to be useful in the sterilization of articles at room temperature, and more effectively, at higher temperatures. These complexes can be placed in a pouch, container, chamber, room or any area capable of being sealed, where they release peroxide vapor which effectively sterilizes the articles. The complexes can be heated to facilitate the release of vapor, and to provide sterilization in less time than that required for room temperature sterilization. The compounds of the present invention are therefore useful in a variety of applications where sterilization is desired. Simply by placing the complex in a sealed area containing an article or articles to be sterilized, sterilization can be achieved. By contrast with prior art methods, there is no need for contact with moisture to provide activation of the hydrogen peroxide.

To confirm that sterilization can be effected using non-aqueous peroxide complexes in less time at lower pressures, the following experiment was performed.

EXAMPLE 11

A self-sterilizing container was assembled as follows: A stainless steel support having $9.2 \times 10^5$ B. subtilis var. niger spores on its surface was placed inside a small PE vial having 20 holes (3/16 "in size) in its surface. The vial was placed in a larger PE vial, which was covered with a gas permeable layer of CSR wrap (SPUNGUARD™). Also included in the larger vial was a second PE vial, also having 20 holes (3/16" in size) in its surface. This vial contained 1 gm urea peroxide in either powder or tablet form. The vial was then sealed in a CSR wrap or TYVEK™ pouch.

The large vials were placed in either a 4.5 L sterilization chamber or a 173 L sterilization chamber. Each container was exposed to 100 torr pressure and 23° C. temperature for 2 hours, as shown in Table 13. The biological test samples were evaluated for sterilization as described in Example 1. The results are included in Table 13.

TABLE 13

Self-Sterilizing Containers With Breathable Window
In Reduced Pressure Conditions

| Temperature | Packaging Type | 4.5 L chamber | 173 L chamber |
| --- | --- | --- | --- |
| 23° C. | Unpackaged powder | – | – |
|  | T/T packaged powder | – | – |
|  | C/C packaged powder | – | – |

These results show that non-aqueous urea peroxide complex included in a container with a breathable barrier provides effective sterilization at 100 torr and room temperature after only 2 hours. These results, when compared with the results in Table 12, demonstrate that the peroxide complexes of the present invention provide sterilization at reduced pressures in less time than that required to effect sterilization at atmospheric pressure.

Thus, the hydrogen peroxide complexes of the present invention can provide effective sterilization in significantly shorter periods of time. In addition, as discussed above, plasma can also be used to enhance the sterilization activity of the hydrogen peroxide vapor. The articles to be sterilized are subjected to a plasma after exposure to the peroxide vapor, and remain in the plasma for a period of time sufficient to effect complete sterilization.

Articles that have been sterilized by exposure to hydrogen peroxide vapor can be exposed to a plasma to remove any residual hydrogen peroxide remaining on the articles. Because the residual hydrogen peroxide is decomposed into non-toxic products during the plasma treatment, the sterilized articles are ready for use following treatment, without the need for any additional steps.

Non-aqueous peroxide complexes are useful in a variety of applications, including as a component of self-sterilizing packaging. In addition, the complexes are suitable for use in various methods for vapor sterilization of articles, such as the method disclosed in U.S. Pat. No. 4,943,414. This patent discloses a process in which a vessel containing a small amount of a vaporizable liquid sterilant solution is attached to a lumen, and the sterilant vaporizes and flows directly into the lumen of the article as the pressure is reduced during the sterilization cycle. The method disclosed in the patent can be modified to allow for use of a non-aqueous peroxide compound. The compound is placed in a vessel and connected to the lumen of the article to be sterilized. The article is then placed within a container and the container evacuated. The lumen of the article and the exterior of the article are contacted by the hydrogen peroxide vapor released from the non-aqueous compound. A plasma can optionally be generated and used to enhance sterilization and/or to remove any residual hydrogen peroxide form the article.

Use of non-aqueous peroxide complexes in the system just described overcomes the disadvantage that the water in the aqueous solution is vaporized faster and precedes the hydrogen peroxide vapor into the lumen. Thus, more effective sterilization is achieved and less time is required to effect sterilization. Hydrogen peroxide complexes such as glycine anhydride are especially advantageous since they release a significant amount of hydrogen peroxide at reduced pressure without the need for additional heating of the complex.

Synthesis of Non-Aqueous Hydrogen Peroxide Complexes

The present invention further provides a process for preparing non-aqueous hydrogen peroxide complexes that are useful as the source in a hydrogen peroxide vapor sterilizer, or as a component of self-sterilizing packaging, as was described above. Of course, the hydrogen peroxide complexes can be used for other applications, such as for bleaching agents, contact lens solutions, catalysts, and other applications which will be well known by those having ordinary skill in the art.

The general procedure for preparing the hydrogen peroxide complexes of this invention is as follows:

(1) Place the reactant material in the chamber.

The material to be reacted with the hydrogen peroxide can be a solid in various forms, (e.g., powder, crystal, film etc., preferably having high surface area to increase the reaction rate). The reactant material can also be present as a solution in water or another solvent, if sufficient time is allowed to evaporate the solvent after the pressure is reduced in the chamber. The material may also be a liquid whose boiling point is higher than that of hydrogen peroxide (150° C.). Since reaction rates are faster at elevated temperature, the chamber is preferably heated whether before or after the reactant composition is introduced. However, the temperature should not be so high that the reactant boils or vaporizes.

The reactant composition may be contained in any container that provides access to the peroxide vapor. If it is in the form of a powder or other form that may be blown about when the chamber is evacuated, then the reactant may be retained in a permeable container, which allows hydrogen peroxide to diffuse into the container.

(2) Evacuate the chamber.

Preferably, the chamber is evacuated to a pressure that is below the vapor pressure of the hydrogen peroxide (which depends on its concentration and temperature), in order to assure that all of the peroxide is in the vapor phase. The vapor pressure increases with increasing temperature and decreases with increasing peroxide concentration. For most of the experiments, the chamber was evacuated to about 0.2 Torr and the temperature was ambient or above.

(3) Generate hydrogen peroxide vapor.

The hydrogen peroxide vapor can be generated from a hydrogen peroxide solution or from a substantially anhydrous hydrogen peroxide complex. The latter yields dry hydrogen peroxide in the vapor state, which is an advantage if either the material to be reacted with the vapor or the complex to be formed is hygroscopic. Another advantage of generating the hydrogen peroxide vapor from a substantially water-free complex is that the percent of hydrogen peroxide in the complex being formed is higher than if the vapor is generated from an aqueous solution of $H_2O_2$. This is probably due to the competition between water molecules and H₂O₂ molecules for bonding sites on the complex when an aqueous solution is used to generate the H₂O₂ vapor.

The peroxide vapor can be generated within the same chamber that houses the reactant material or in another chamber separated from it by a vacuum valve.

(4) React the reactant material with hydrogen peroxide.

The time required for the reaction depends, of course, on the reaction rate of the reactant with hydrogen peroxide. It can be empirically determined by monitoring the pressure, which decreases during the binding of peroxide to the reactant material. Typically, the reaction time is about 5–30 minutes. The concentration of vaporized hydrogen peroxide and the weight of the starting material determine the weight percentage of peroxide in the final reaction product. As the weight ratio of reactant to hydrogen peroxide increases, the weight percentage of hydrogen peroxide in the complex decreases. The reaction can be repeated multiple times to increase the concentration of hydrogen peroxide in the complex.

(5) Evacuate the chamber again.

At the end of the reaction period, the chamber is further evacuated to about 2 Torr to remove any unreacted hydrogen peroxide.

(6) Vent the chamber and retrieve the hydrogen peroxide complex.

The mechanism by which the hydrogen peroxide forms a complex with the reactant material is not completely understood. The formation of the complex is believed to involve hydrogen bond formation between the hydrogen peroxide and electron-rich functional groups containing oxygen and/or nitrogen on the reactant material. It is not known if this is the only mode of binding; however, materials with a wide range of functional groups have been found to form complexes with hydrogen peroxide.

The advantages of the vapor phase reaction over earlier methods of hydrogen peroxide complex formation include:

1. The ratio of hydrogen peroxide to reactant material can be accurately controlled by varying the amount of hydrogen peroxide present in the vapor state or the amount of reactant material exposed to the vapor.

2. The need to remove solvent from the reaction product is eliminated.

3. Peroxide complexes can be formed that are liquid or solids, such as powders, crystals, films, etc.

4. Peroxide complexes of hygroscopic materials can be prepared.

The synthesis of the non-aqueous peroxide complexes according to the present invention is further described in the following examples. Many of these compounds have utility as catalysts, in addition to having the utilities described in greater detail herein, as will be readily appreciated by those having ordinary skill in the art. The examples represent embodiments of the compositions and processes of the invention, but they are not in any way intended to limit the scope of the invention.

EXAMPLE 12

A hydrogen peroxide complex of glycine anhydride was prepared as follows: A 1.0 gram sample of glycine anhydride (Aldrich Chemical Co., Milwaukee, Wis.) was placed in an aluminum tray in a 173 liter chamber maintained at a temperature of 45° C. The top of the aluminum tray was covered with TYVEK™ nonwoven fabric, which prevented the glycine anhydride from coming out of the tray when the pressure in the chamber was reduced but was breathable and did not absorb hydrogen peroxide. The chamber door was closed and the pressure in the chamber was reduced to 0.2 Torr by evacuating the chamber with a vacuum pump. A hydrogen peroxide concentration of 10 mg/liter was created by evaporation of an appropriate volume of a 70% aqueous solution of hydrogen peroxide (FMC Corp., Philadelphia, Pa.) into the chamber. The hydrogen peroxide vapor was maintained in contact with the glycine anhydride for 20 minutes. At the end of the reaction period, the chamber pressure was reduced to 2 Torr and then returned to atmospheric pressure. The reaction product was removed from the chamber and analyzed for weight percent hydrogen peroxide by the following iodometric titration reactions.

$$H_2O_2+2KI+H_2SO_4 \rightarrow I_2+K_2SO_4+2H_2O$$

$$I_2+2Na_2S_2O_3 \rightarrow Na_2S_4O_6+2NaI$$

A starch indicator was used in the iodine-sodium thiosulfate titration reaction to enhance the color change at the end point. The percentage by weight of hydrogen peroxide was calculated by the following equation:

$$wt\ \%\ H_2O_2=[(ml\ of\ Na_2S_2O_3)*(normality\ of\ Na_2S_2O_3)*1.7]/(sample\ weight\ in\ grams)$$

The weight percentage of hydrogen peroxide in the glycine anhydride complex was found to be 24.3%.

EXAMPLE 13

The hydrogen peroxide complexes of a wide variety of organic and inorganic complexes were prepared using the procedure of Example 12. In each case, the reaction conditions were the same as those in Example 12, except 1.0 gram of each one of the compounds presented in Table 14 was used in place of glycine anhydride.

TABLE 14

COMPOUNDS EVALUATED AND WEIGHT PERCENT HYDROGEN PEROXIDE
PRESENT IN COMPLEXES FORMED BY VAPOR PHASE SYNTHESIS PROCESS

| Chemical Name | Chemical Structure | Wt % After Peroxide Treatment | Category |
|---|---|---|---|
| Poly(vinyl alcohol) | [—CH₂CH(OH)—]ₙ | 18.9% | Alcohol |
| Poly(vinyl methyl ether) | [—CH₂CH(OCH₃)—]ₙ | 22.0% | Ether |
| Poly(vinyl methyl Ketone) | [—CH₂—CH(COCH₃)—]ₙ | 13.9% | Ketone |
| Poly(acrylic acid) | [—CH₂CH(COOH)—]ₙ | 5.1% | Acid |
| Glycine | H₂C(NH₂)(COOH) | 20.7% | Amino Acid |

TABLE 14-continued

COMPOUNDS EVALUATED AND WEIGHT PERCENT HYDROGEN PEROXIDE
PRESENT IN COMPLEXES FORMED BY VAPOR PHASE SYNTHESIS PROCESS

| Chemical Name | Chemical Structure | Wt % After Peroxide Treatment | Category |
|---|---|---|---|
| L-Histidine | [N=CHNHCH=C]$CH_2CH(NH_2)COOH$ | 14.1% | Amino Acid |
| Poly(vinyl acetate) | [$-CH_2CH(OCOCH_3)-$]$_n$ | 9.1% | Ester |
| Cellulose acetate | | 10.9% | Ester |
| Sodium alginate | | 27.7% | Organic Salt |
| Cellulose sulfate, sodium salt | | 18.2% | Organic Salt |
| Poly(4-Vinylpyridine) | [$-CH_2CH(p-C_5H_4N)-$]$_n$ | 21.8% | Aromatic amine |
| Histamine | [N=CHNHCH=C—]$CH_2CH_2(NH_2)$ | 13.2% | Amine |
| Propionamide | $(C_2H_5)CONH_2$ | 31.8% | Amide |
| Urea | $(H_2N)_2CO$ | 17.9% | Urea |
| 1,3-dimethylurea | $(H_3C)HNCONH(CH_3)$ | 31.7% | Urea |
| Biuret | $(H_2N)CO(NH)CO(NH_2)$ | 13.7% | Biuret |
| Polyacrylamide | [$-CH_2CH(CONH_2)-$]$_n$ | 30.1% | Polyamide |
| Polyvinylpyrrolidone | [$-CH_2CH(-N(CH_2)_3CO)-$]$_n$ | 29.9% | Polyamide |
| Nylon 6 | [$-NH(CH_2)_5CO-$]$_n$ | 17.1% | Polyamide |
| Nylon 6,6 film | [$-NH(CH_2)_6NHCO(CH_2)_4CO-$]$_n$ | 16.6% | Polyamide |
| Polyetherpolyurethane | [$-RHNCOOR'-$]$_n$ | 9.5% | Polyurethane |
| Sodium carbonate | $Na_2CO_3$ | 14.3% | Inorganic |
| Potassium carbonate | $K_2CO_3$ | 33.9% | Inorganic |
| Rubidium carbonate | $Rb_2CO_3$ | 37.0% | Inorganic |
| Calcium hydroxide | $Ca(OH)_2$ | 23.4% | Inorganic |
| Sodium bicarbonate | $NaHCO_3$ | 10.7% | Inorganic |
| Tetrasodium pyrophosphate | $Na_4P_2O_7$ | 18.9% | Inorganic |

The organic complexes formed cover the following range of functional groups that are capable of forming hydrogen bonds with hydrogen peroxide: alcohols, ethers, ketones, acids, amino acids, esters, organic salts, amines, amides, polyamides, polyurethanes, ureas, and biuret. The inorganic complexes include carbonates with sodium, potassium, and rubidium cations, as well as sodium bicarbonate. In addition, the hydrogen peroxide complexes of calcium hydroxide and tetrasodium pyrophosphate were also prepared. The starting materials were finely divided powers or slightly larger crystalline materials, except for nylon 6,6, which was processed as a film with a thickness of 0.12 mm, and polyvinyl methyl ether, which was a 50% by weight aqueous solution.

The hydrogen peroxide complexes obtained with these materials under the test conditions were solids, except for polyvinylpyrrolidone, histamine, poly(vinyl methyl ether), poly(vinyl methyl ketone),propionamide, and 1,3-dimethylurea. The 1,3-dimethylurea and propionamide hydrogen peroxide complexes were free flowing liquids that were easily handled in the vapor phase synthesis process, since no solvent needed to be removed to obtain the final product. The histamine, polyvinylpyrrolidone, poly(vinyl methyl ether), and poly(vinyl methyl ketone) complexes were gummy materials that were not as easy to handle.

Examples 14 and 15 describe additional studies with polyvinylpyrrolidone under different process conditions to obtain the peroxide complex as a free flowing solid product.

EXAMPLE 14

Hydrogen peroxide complexes with polyvinylpyrrolidone were prepared in which the percent hydrogen peroxide in the polyvinylpyrrolidone complex was varied by changing the ratio of the weight of polyvinylpyrrolidone to the concentration of hydrogen peroxide in the vapor state. The conditions in these tests were identical to those in Example 12, except the weight of polyvinylpyrrolidone was increased from 1.0 gram to 3.0 grams to 5.0 grams. In all tests, the concentration of hydrogen peroxide was held constant at 10.0 mg/liter of chamber volume. The results of these tests are presented in Table 15.

EXAMPLE 15

A hydrogen peroxide complex of PVP was prepared in which the hydrogen peroxide was delivered from a complex of hydrogen peroxide with urea. When hydrogen peroxide is delivered in this manner, it is substantially water free. In this test, 5 grams of PVP was placed in the reaction chamber and 10 mg $H_2O_2$/liter of chamber volume was delivered into the reaction chamber by heating about 7 grams of a 35% complex of $H_2O_2$ with urea to a temperature of about 110° C. for approximately 5 minutes. The rest of the conditions in this test were the same as those in Example 12. The percentage hydrogen peroxide in the PVP complex and the physical state of the complex are presented in Table 15.

TABLE 15

EFFECT OF RATIO OF POLYVINYLPYRROLIDONE TO HYDROGEN PEROXIDE IN THE VAPOR STATE ON % HYDROGEN PEROXIDE IN COMPLEX AND PHYSICAL STATE OF PRODUCT

|        | Weight PVP (g) | Wt % $H_2O_2$ in Complex | Physical State of Product |
|--------|----------------|--------------------------|---------------------------|
| Ex. 14 | 1              | 29.9                     | Soft gummy product        |
|        | 3              | 23.5                     | Hard gummy product        |
|        | 5              | 17.7                     | Free flowing solid        |
| Ex. 15 | 5              | 19.7                     | Free flowing solid        |

The results of these tests demonstrate that a free flowing solid can be obtained with the PVP hydrogen peroxide complex by controlling the ratio of PVP to hydrogen peroxide in the vapor state and, alternatively, by using a substantially water-free hydrogen peroxide vapor source.

We claim:

1. A process for preparing a substantially non-aqueous hydrogen peroxide complex, comprising the steps of:

evacuating a chamber that contains a composition capable of reacting with hydrogen peroxide vapor to a pressure that is below the vapor pressure of said hydrogen peroxide vapor; then introducing the hydrogen peroxide vapor into the chamber, wherein the hydrogen peroxide vapor reacts with the composition to form the hydrogen peroxide complex.

2. The process of claim 1, wherein the composition is selected from the group consisting of an alcohol, an ether, a ketone, an acid, an amino acid, an ester, an organic salt, an amine, an amide, urea, biuret, a polyamide, a polyurethane, an alkali metal carbonate, a hydroxide, and tetrasodium pyrophosphate.

3. The process of claim 1, wherein the composition is poly(vinyl alcohol).

4. The process of claim 1, wherein the composition is poly(vinyl methyl ether).

5. The process of claim 1, wherein the composition is poly(vinyl methyl ketone).

6. The process of claim 1, wherein the composition is poly(acrylic acid).

7. The process of claim 1, wherein the composition is glycine or L-histidine.

8. The process of claim 1, wherein the composition is poly(vinyl acetate) or cellulose acetate.

9. The process of claim 1, wherein the composition is sodium alginate or cellulose sulfate, sodium salt.

10. The process of claim 1, wherein the composition is a histamine.

11. The process of claim 1, wherein the composition is glycine anhydride.

12. The process of claim 1, wherein the composition is propionamide.

13. The process of claim 1, wherein the composition is polyacrylamide.

14. The process of claim 1, wherein the composition is selected from the group consisting of polyvinylpyrrolidone, poly(4-vinylpyridine), nylon 6, and nylon 6,6 film.

15. The process of claim 1, wherein the composition is polyetherpolyurethane.

16. The process of claim 1, wherein the composition is selected from the group consisting of sodium carbonate, potassium carbonate, rubidium carbonate, and sodium bicarbonate.

17. The process of claim 1, wherein the composition is calcium hydroxide.

18. The process of claim 1, wherein the composition is 1,3 dimethylurea.

19. The process of claim 1, in which the hydrogen peroxide vapor is substantially anhydrous.

* * * * *